(12) United States Patent
Parsons (10) Patent No.: US 9,675,077 B2
(45) Date of Patent: Jun. 13, 2017

(54) COMPOSITION COMPRISING ANTIMICROBIAL METAL IONS AND A QUATERNARY CATIONIC SURFACTANT

(75) Inventor: David Parsons, Flintshire (GB)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 0 days.

(21) Appl. No.: 14/114,517

(22) PCT Filed: Apr. 5, 2012

(86) PCT No.: PCT/GB2012/000329
§ 371 (c)(1),
(2), (4) Date: Nov. 14, 2013

(87) PCT Pub. No.: WO2012/136968
PCT Pub. Date: Oct. 11, 2012

(65) Prior Publication Data
US 2014/0056993 A1     Feb. 27, 2014

(30) Foreign Application Priority Data
Apr. 6, 2011 (GB) .................................. 1105829.4

(51) Int. Cl.
| | | |
|---|---|---|
| *A01N 59/16* | (2006.01) | |
| *A01N 33/12* | (2006.01) | |
| *A61K 31/14* | (2006.01) | |
| *A61K 31/198* | (2006.01) | |
| *A61K 33/24* | (2006.01) | |
| *A61K 33/26* | (2006.01) | |
| *A61K 33/30* | (2006.01) | |
| *A61K 33/32* | (2006.01) | |
| *A61K 33/34* | (2006.01) | |
| *A61K 33/38* | (2006.01) | |
| *A01N 37/44* | (2006.01) | |
| *A01N 59/20* | (2006.01) | |
| *A61K 9/00* | (2006.01) | |
| *A61K 9/06* | (2006.01) | |

(52) U.S. Cl.
CPC ............. *A01N 59/16* (2013.01); *A01N 33/12* (2013.01); *A01N 37/44* (2013.01); *A01N 59/20* (2013.01); *A61K 9/0014* (2013.01); *A61K 9/06* (2013.01); *A61K 31/14* (2013.01); *A61K 31/198* (2013.01); *A61K 33/24* (2013.01); *A61K 33/245* (2013.01); *A61K 33/26* (2013.01); *A61K 33/30* (2013.01); *A61K 33/32* (2013.01); *A61K 33/34* (2013.01); *A61K 33/38* (2013.01)

(58) Field of Classification Search
CPC ........ A01N 39/16; A01N 33/12; A01N 37/44; A01N 59/20; A61K 31/14; A61K 31/198; A61K 9/0014; A61K 9/06; A61K 33/24; A61K 33/245; A61K 33/26; A61K 33/30; A61K 33/32; A61K 33/34; A61K 33/38
See application file for complete search history.

(56) References Cited

U.S. PATENT DOCUMENTS

| | | | |
|---|---|---|---|
| 6,753,063 B1 * | 6/2004 | Pung et al. | .................... 428/152 |
| 7,033,511 B2 * | 4/2006 | Zawada | ................. A01N 33/12 |
| | | | 210/764 |
| 2006/0051430 A1 | 3/2006 | Arata et al. | |
| 2006/0115440 A1 * | 6/2006 | Arata et al. | ..................... 424/65 |
| 2006/0254988 A1 | 11/2006 | Frampton | |
| 2007/0134136 A1 | 6/2007 | Polyakov | |
| 2008/0112920 A1 | 5/2008 | Chia | |

FOREIGN PATENT DOCUMENTS

| | | |
|---|---|---|
| CN | 101076251 A | 11/2007 |
| EP | 1925719 | 5/2008 |
| WO | WO2005020915 | 3/2005 |
| WO | WO2006029213 | 3/2006 |
| WO | WO2009130608 | 10/2009 |

OTHER PUBLICATIONS

Smith & Nephew et al: "OTC Medication Information: Dermal Wound Cleanser—benzethonium chloride spray", Dec. 17, 2009 (Dec. 17, 2009), pp. 1-9.
Gordon Ramage et al: "Inhibition on Candida albicans biofilm formation using divalent cation chelators (EDTA)", Mycopathologia, Kluwer Academic Publishers, DO, vol. 164, No. 6, Oct. 2, 2007 (Oct. 2, 2007), pp. 301-306.
Percival Steven L et al: "Tetrasodium EDTA as a novel central venous catheter lock solution against biofilm"Database BIOSIS, [Online] Jun. 1, 2005 (Jun. 1, 2005).
Nagai et al: "Suppressive effects of EDTA for Pseudomonas aeruginosa products biofilm", STN CAPLUS, Jan. 1, 1996.
Chinese Patent Application No. 201280027537.6 Chinese Third Office Action dated Mar. 2, 2016 (English translation provided).

\* cited by examiner

*Primary Examiner* — Ali Soroush
(74) *Attorney, Agent, or Firm* — Wilson Sonsini Goodrich & Rosati (57) ABSTRACT

The present invention relates to an antimicrobial composition suitable for use on skin and wounds comprising a source of an antimicrobial metal ion and a quaternary cationic surfactant.

17 Claims, 8 Drawing Sheets

| Solutions | | | | | | |
|---|---|---|---|---|---|---|
| Ag | 0.0001 | 0.02 | 0.0001 | 0.02 | 0.0001 | 0.02 |
| EDTA | 0.02 | 0.02 | 0.02 | 0.02 | 0.02 | 0.02 |
| BeCl | 0 | 0 | 0.1 | 0.1 | 1 | 1 |
| pH | 4 | 4 | 4 | 4 | 4 | 4 |
| Growth /6 | 4 | 0 | 0 | 1 | 0 | 1 |
| Ag | 0.0001 | 0.02 | 0.0001 | 0.02 | 0.0001 | 0.02 |
| EDTA | 1 | 1 | 1 | 1 | 1 | 1 |
| BeCl | 0 | 0 | 0.1 | 0.1 | 1 | 1 |
| pH | 4 | 4 | 4 | 4 | 4 | 4 |
| Growth /6 | 4 | 2 | 1 | 1 | 2 | 1 |
| Ag | 0.0001 | 0.02 | 0.0001 | 0.02 | 0.0001 | 0.02 |
| EDTA | 0.02 | 0.02 | 0.02 | 0.02 | 0.02 | 0.02 |
| BeCl | 0 | 0 | 0.1 | 0.1 | 1 | 1 |
| pH | 8 | 8 | 8 | 8 | 8 | 8 |
| Growth /6 | 6 | 0 | 0 | 0 | 1 | 2 |
| Ag | 0.0001 | 0.02 | 0.0001 | 0.02 | 0.0001 | 0.02 |
| EDTA | 1 | 1 | 1 | 1 | 1 | 1 |
| BeCl | 0 | 0 | 0.1 | 0.1 | 1 | 1 |
| pH | 8 | 8 | 8 | 8 | 8 | 8 |
| Growth /6 | 6 | 0 | 1 | 0 | 0 | 0 |

| Gels | | | | | | |
|---|---|---|---|---|---|---|
| Ag | 0.0001 | 0.02 | 0.0001 | 0.02 | 0.0001 | 0.02 |
| EDTA | 0.02 | 0.02 | 0.02 | 0.02 | 0.02 | 0.02 |
| BeCl | 0 | 0 | 0.1 | 0.1 | 1 | 1 |
| pH | 4 | 4 | 4 | 4 | 4 | 4 |
| Growth /6 | 6 | 0 | 1 | 0 | 0 | 1 |
| Ag | 0.0001 | 0.02 | 0.0001 | 0.02 | 0.0001 | 0.02 |
| EDTA | 1 | 1 | 1 | 1 | 1 | 1 |
| BeCl | 0 | 0 | 0.1 | 0.1 | 1 | 1 |
| pH | 4 | 4 | 4 | 4 | 4 | 4 |
| Growth /6 | 4 | 0 | 0 | 0 | 0 | 0 |
| Ag | 0.0001 | 0.02 | 0.0001 | 0.02 | 0.0001 | 0.02 |
| EDTA | 0.02 | 0.02 | 0.02 | 0.02 | 0.02 | 0.02 |
| BeCl | 0 | 0 | 0.1 | 0.1 | 1 | 1 |
| pH | 8 | 8 | 8 | 8 | 8 | 8 |
| Growth /6 | 6 | 0 | 0 | 0 | 0 | 0 |
| Ag | 0.0001 | 0.02 | 0.0001 | 0.02 | 0.0001 | 0.02 |
| EDTA | 1 | 1 | 1 | 1 | 1 | 1 |
| BeCl | 0 | 0 | 0.1 | 0.1 | 1 | 1 |
| pH | 8 | 8 | 8 | 8 | 8 | 8 |
| Growth /6 | 6 | 0 | 1 | 0 | 0 | 0 |

FIG. 3

COMPOSITION COMPRISING ANTIMICROBIAL METAL IONS AND A QUATERNARY CATIONIC SURFACTANT

This application is a U.S. national phase application of PCT/GB2012/000329, filed Apr. 5, 2012; which claims the benefit of priority of GB 1105829.4, filed Apr. 6, 2011, both of which are herein incorporated by reference in their entirety.

This invention relates to an antimicrobial composition which can be applied to skin, wounds, cuts, abrasions or burns for the prevention or treatment of infections or to wound dressings and the like for application to skin, wounds, cuts, abrasions or burns. More particularly the invention relates to a composition capable of providing effective antimicrobial activity while at the same time avoiding wound and skin irritation and retardation of wound healing.

Overuse of antibiotics and the associated increase in bacterial resistance is impacting the efficacy of antibiotics in the treatment of wound infection. Effective alternatives to antibiotics are thus desirable.

Topical antimicrobial materials and preparations containing them have long been recognised as playing an important part in minimising the opportunity for skin and wound infections. Non-antibiotic antimicrobials are non-selective chemical agents that can be safe to use on living tissue. Molecular iodine, ionic silver and oxidising agents such as sodium hypochlorite and chlorine dioxide have been recognised as antimicrobial agents with effectiveness against a wide range of micro-organisms. There are however several barriers to making an effective antimicrobial composition for application to wounds based on such agents. One problem is that these antimicrobial agents tend to react with organic materials found in the wound other than the intended microbial targets. This means that to be effective, antimicrobial agents need to be included in treatment compositions at high levels, which may cause undesirable side effects with prolonged use such as cell toxicity, hypersensitivity reactions, skin staining and systemic effects. Such side effects are further described in "In vitro cytotoxity of silver: implication for clinical wound care". Poon V K, Burd A. Burns. 2004 March; 30(2):140-7, "A review of iodine toxicity reports". Pennington J A. J Am Diet Assoc. 1990 November; 90(11):1571-81 and "Topical antimicrobial toxicity". Lineaweaver W, Howard R, Soucy D, McMorris S, Freeman J, Crain C, Robertson J, Rumley T. Arch Surg. 1985 March; 120(3):267-70.

There is therefore a need for a means to make treatment compositions effective without simply increasing the level of antimicrobial agent included in the composition. It has also been recognised that wound bacteria often exist in biofilms and that these are more difficult to treat than their planktonic counterparts.

We have found that it is possible to increase the effectiveness of antimicrobial metal ions by including a quaternary cationic surfactant in the formulation.

Accordingly a first aspect of the invention provides an antimicrobial composition suitable for use on skin and wounds comprising a source of antimicrobial metal ion and a quaternary cationic surfactant.

The presence of the quaternary cationic surfactant enhances the effect of the antimicrobial metal ion so that the performance of the antimicrobial metal ion is improved. For instance the presence of the quaternary cationic surfactant can increase the speed at which the antimicrobial metal ion works By the term antimicrobial it is meant a substance that inhibits the growth of, or kills, micro-organisms from the taxonomical kingdoms of bacteria, fungi and protozoa. An effective antimicrobial composition is therefore one which is used to reduce and prevent the spread and proliferation of micro-organisms in a specific application. In wound care this can be interpreted in terms of control of cross-infection, prevention or elimination of infection and the reduction of recalcitrant bioburden that can cause delayed healing and chronicity.

We have also found that it is possible to prepare a composition which includes a quaternary cationic surfactant which is effective under the conditions of pH normally found in a wound.

Accordingly a second aspect of the invention provides a composition suitable for use on wounds comprising a quaternary cationic surfactant at a pH of 4 to 8.

The compositions according to a first aspect of the invention comprise an antimicrobial agent, preferably a metal ion for example silver, iron, nickel, copper, chromium, manganese, gold, gallium, magnesium, mercury, lead, aluminium, lead, zinc, bismuth, tin and palladium. Preferably the metal ion is silver. The antimicrobial agent is preferably included in the composition at a level of from 0.01% to 10% by weight, more preferably 0.1% to 5% and even more preferably 0.5% to 1.5% by weight or 1% to 5%. If the composition is in aqueous solution the antimicrobial metal ion is preferably in an aqueous solution comprising from 0.00001% to 1.0% by weight or more preferably 0.0001% to 0.1%, even more preferably 0.0001% to 0.02% by weight or 0.001% to 1.0% by weight.

The compositions according to the invention comprise a cationic surfactant. The cationic surfactant can be a quaternary ammonium salt, an alkyl pyridinium salt, an alkyl imidazolium salt, an alkyl morpholinium salt, a benzethonium salt or an ethoxylated quaternary ammonium salt or mixtures thereof. Preferably where the salt is a quaternary ammonium salt, it is selected from the group of monoalkyl trimethyl ammonium salts, dialkyl dimethyl ammonium salts and monoalkyl monobenzyl dimethyl ammonium salts. Preferably the cationic surfactant is a quaternary cationic surfactant and more preferably a quaternary ammonium surfactant. Preferably the cationic surfactant is selected from the group of benzethonium, benzalkonium, dimethyldialkylonium, alkylpyridinium and alkyltrimethylammonium cations with any counter ion, for example: bromide, chloride, acetate or methyl sulphate. Preferably the quaternary cationic surfactant is present at a level of more than or equal to 0.025% by weight, more preferably from 0.05% to 4% by weight and more preferably from 0.5% to 2% by weight.

The pH of the composition is preferably between 4 and 8, more preferably between 4 and 6 and most preferably between 4.5 and 5.5. The desired pH may be achieved by incorporating buffering agents in the composition. Examples of buffering agents which may be included are citric acid/di-sodium hydrogen phosphate, citric acid/sodium citrate, acetic acid/sodium acetate. The buffering agent may conveniently be present in an amount of about 0.5% to 2% by weight of the composition so as to provide an isotonic composition The composition preferably comprises ethylenediaminetetra-acetic acid (EDTA). EDTA is preferably present as the di-, tri- or tetra-basic salts of EDTA. We have found that these salts enhance the antimicrobial effect of the ionic metal in disrupting biofilm. For example we have found that EDTA at concentrations of 0.25-0.5% weight by volume was effective in making a range of microorganisms in the biofilm state vulnerable to antimicrobial agents.

EDTA is preferably present in the compositions of the present invention at a level of 0.1% to 4% by weight of the composition, more preferably less than 2% by weight, more preferably 0.2 to 1% by weight.

The compositions of the present invention may be in the form of a solution which can be used as a spray to be applied to dressing materials or a solution dip into which dressing materials can be immersed, or in the form of thin soluble films which can be laminated to wound dressings or used along with a separate dressing in the form of a kit. Alternatively the compositions can be in the form of a soft semi-solid such as a gel, foam or creme which maintains a moist wound healing environment and promotes natural healing. A soft semi-solid formulation gives the advantage of being able to flow into a wound to form an intimate contact with the wound bed and provide antimicrobial effects to the entire surface of a wound. Preferably the formulation has a high enough viscosity that it does not flow out of a wound onto other tissues. Preferably the pH of the formulation is buffered at around 5.5 as this does not alter the pH balance of the peri-wound tissue and therefore protects it. The compositions of the invention may also be present as a dry powder spray.

The following examples are illustrative of the present invention.

The data relevant to the examples is represented in the accompanying drawings which show.

EXAMPLE 1

Quaternary Cationic Surfactant Enhancement of Silver Efficacy

Method: The MBEC Assay System using the Calgary Biofilm Device provides an assay for screening antibiotics and biocides for activity against bacterial biofilms. The system involves a reactor for the formation of 96 equivalent biofilms. The MBEC Assay System is suited to determination of MBEC values (Minimum Biofilm Eradication Concentration) and other related values. A description of the system and method is given in "The MBEC Assay System: Multiple Equivalent Biofilms for Antibiotic and Biocide Susceptibility Testing" by Howard Ceri, Merle Olson, Douglas Morck, Douglas Storey, Ronald Read, Andre Buret and Barbara Olson, 2001 Methods in Enzymology Vol 337, [25] p377 and "The Calgary Biofilm Device: New Technology for Rapid Determination of Antibiotic Susceptibilities of Bacterial Biofilms" Ceri, Olson, Stremick, Read, Morck and Buret Journal of Clinical Microbiology, June 1999, Vol 37, No. 6, p 1771-1776.

Biofilms were grown on the pegs of 96-well plate lids (Nunc-TSP parts 445497 and 167008, Thermo Fisher Scientific Inc); these were then thoroughly rinsed in purified water. Into a fresh plate, using aseptic techniques and filter sterilised solutions, aliquots of an aqueous silver nitrate solution, various quaternary cationic surfactant aqueous solutions and purified water were pipetted to give a matrix of 100 µl test samples of various silver and surfactant concentrations. The biofilm covered plate lids were then replaced and left in contact with the test solution for either 30 minutes, 2 or 4 hours. After this time the lids were removed and any residual test agent was removed from the pegs by rinsing in sterile normal saline solution (0.85% w/w NaCl). The residual biofilms were then physically removed from the pegs by the established sonication method. The released and still vaible bacteria where then grown-on in their planktonic form for 24 hours in a new plate in which the wells contained a growth medium. The concentration of surviving bacteria released from the pegs was then estimated by turbidity measurement on an optical plate reader. Although optical densities were recorded, a simple grey scale representation was adequate for interpretation.

Tested silver ion concentrations ranged from 1.625 µg/ml to 200 µg/ml, doubling in concentration between successive samples. The cationic surfactants tested were benzethonium benzalkonium chloride, dimethyldialkylammonium chloride, cetyltrimethylammonium bromide and cetylpyridinium chloride at concentrations ranging from 31.25 µg/ml to 2000 µg/ml also doubling in concentration between successive samples.

Figure 1A:
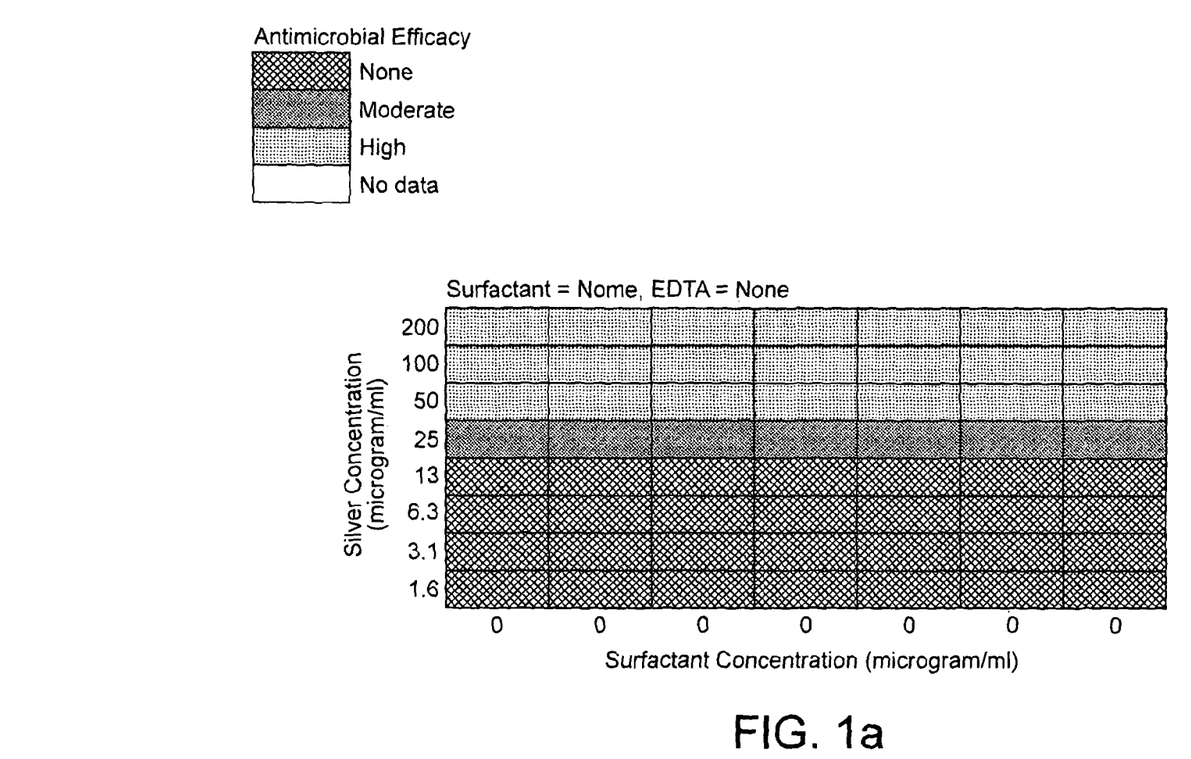
FIGS. 1a, 1b, 1c and 1d show grey scales representing antimicrobial efficacies of a range of silver concentrations against a range of surfactant concentrations and a range of surfactants and optional ingredients.
Figure 1B:
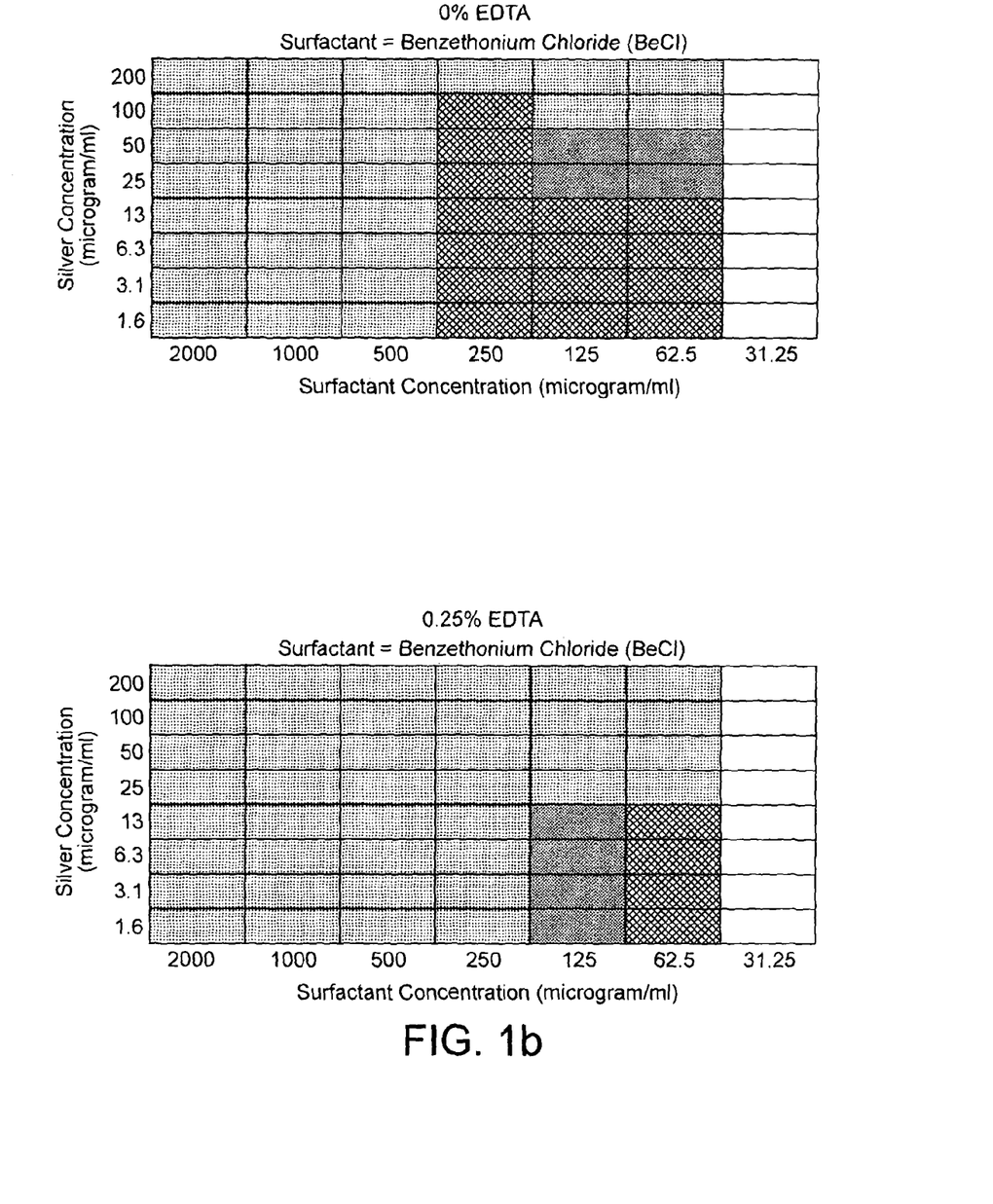
Figure 1C:
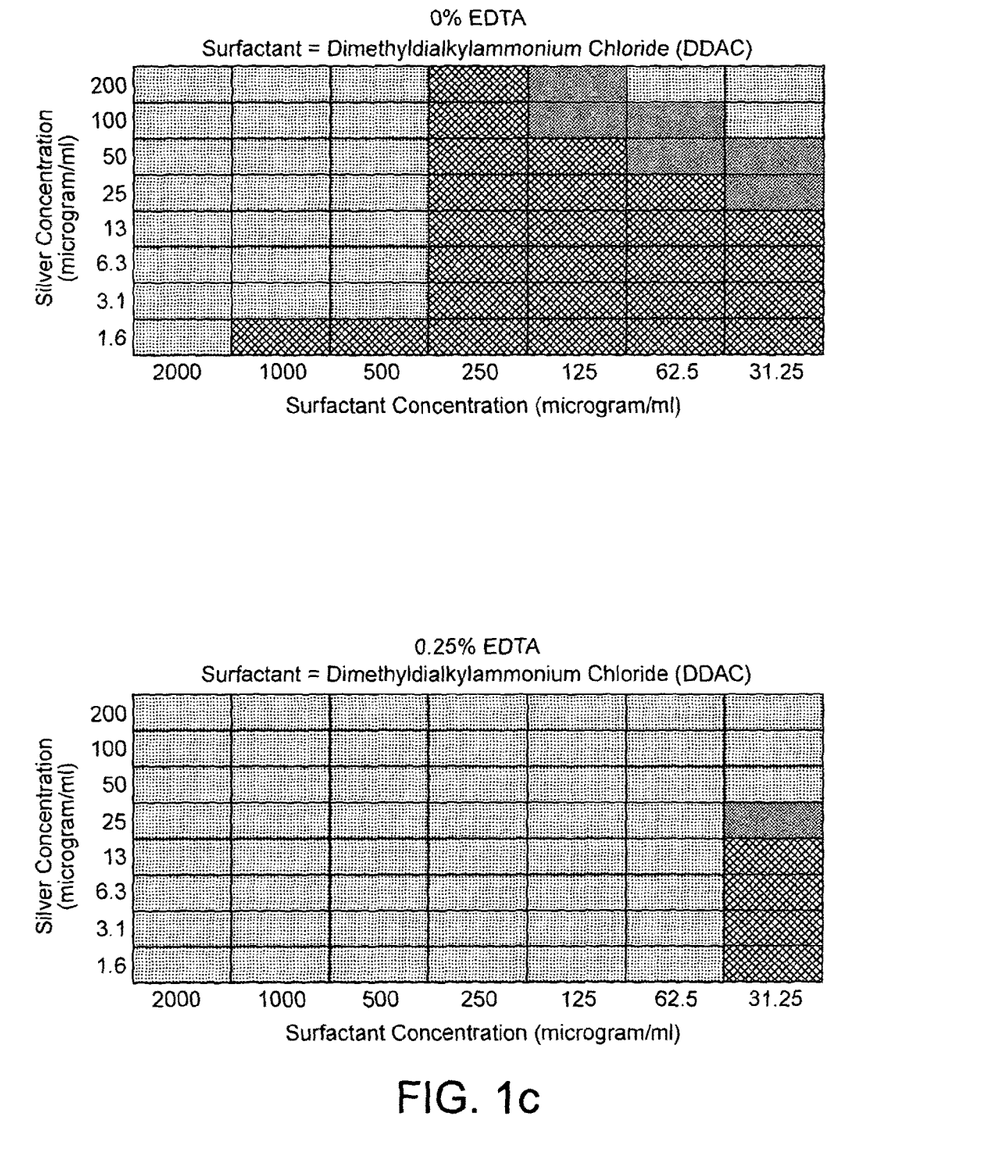
Figure 1D:
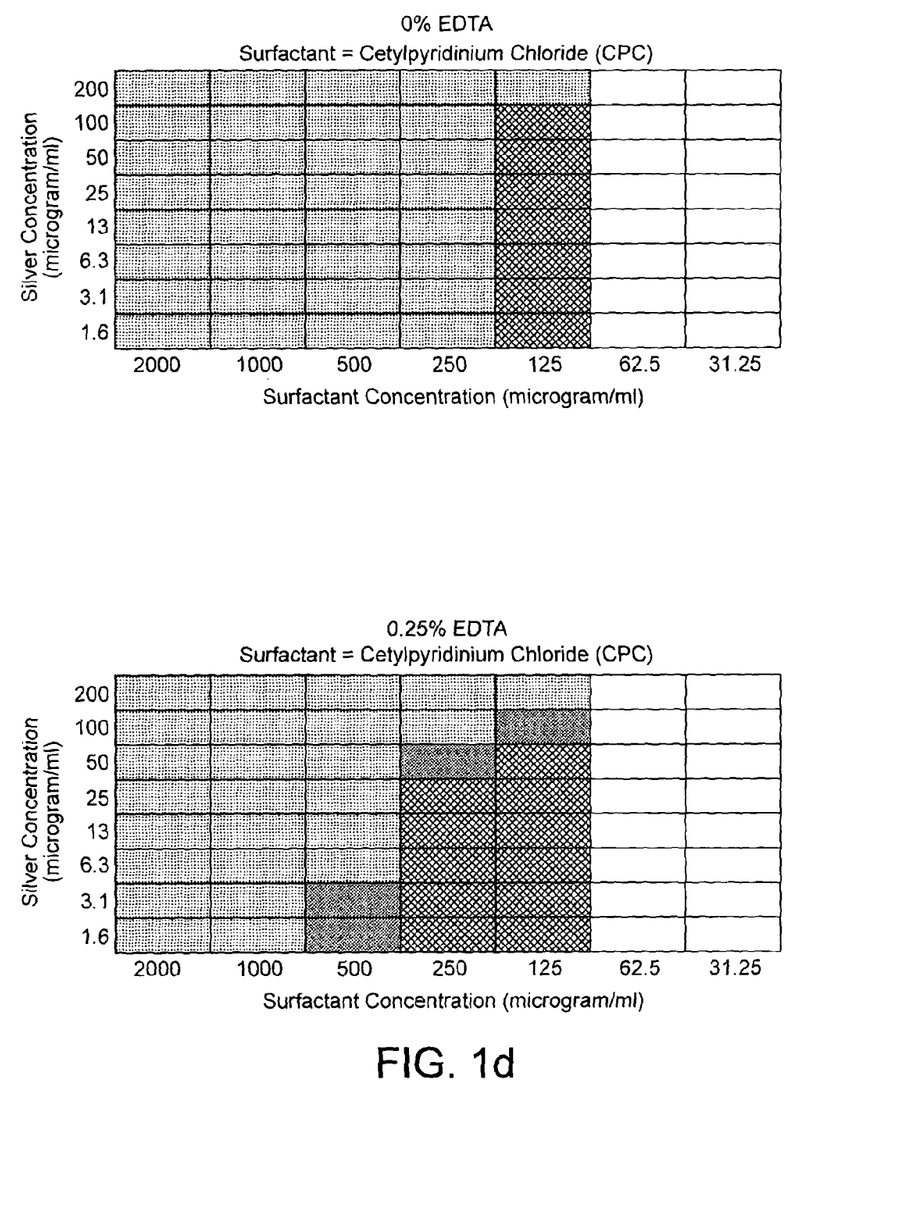

Results: The results are presented by the charts in FIG. 1a and by the lefthand diagram in FIGS. 1b, 1c and 1d. The grey scale represents the antimicrobial efficacy. The higher the efficacy the lighter the shade of grey so that no antimicrobial efficacy is represented by black and high antimicrobial efficacy is represented by light grey. Positive synergies are represented by a shift to a paler position on the grey scale from the experimental control (no surfactant) presented in FIG. 1a. In the figures silver concentration is shown on the y-axis and surfactant concentration is shown on the x-axis.

These results show the concentration ranges where synergy was observed. All cationic surfactants assayed showed synergy with ionic silver above a specific critical concentration for each surfactant. Below this critical concentration inhibition of the antimicrobial effect of silver ions was observed.

EXAMPLE 2

EDTA and Quaternary Cationic Surfactant Enhancement of Silver Efficacy

Method: As Example 1 but with each test solution also containing 0.25% w/w di-sodium ethylenediaminetetra-acetic acid salt.

Results: The results are presented in FIGS. 1b, 1c and 1d by the diagram on the righthand side. Diagrams on the lefthand side are the corresponding experiments without EDTA.

These results show that EDTA further enhances the synergistic antimicrobial activity of the cationic surfactant and the metal ion.

EXAMPLE 3

Enhancement of Antimicrobial Efficacy of Examples of Silver Containing Wound Dressings The depth to which an antimicrobial effect on an agar gel containing *Staphylococcus aureus* was assessed for different types of treated and untreated silver containing wound dressings.

Materials:
Test Dressings:
AQUACEL Ag (5×5 cm), batch 9L019035, absorbent, gelling, fibrous-felt dressing containing 1.2% w/w ionic silver.
Allevyn Ag Non-adhesive, batch 0935, absorbent foam dressing containing silver sulphadiazine.
Silvercel Hydro-alginate, batch, 37923, a dressing comprised of a mixed alginate and silver-coated nylon fibrous pad wrapped in a perforated ethylene methyl acrylate film.
Sorbsan Silver—Plus, batch 012035, an absorbent non-woven alginate pad impregnated with silver, bonded to a secondary absorbent viscose layer.
All of the above treated with di-sodium EDTA and benzethonium chloride.
Microbiological Media:
Maximal Recovery Diluent (MRD)
Pre-dried Tryptone Soy Agar (TSA) plates
0.85% Saline Solution
Molten Tryptone Soy Agar (TSA)
Industrial Denatured Alcohol (IDA)
Sterile Deionised Water (SDW)
Microbial Challenge: *Staphylococcus aureus* NCIMB 9518

Methods: Two 3.75 cm diameter circular samples were aseptically cut from each dressing. One of each sample was placed into a sterile Petri dish for later testing. The remaining sample was treated with a solution according to the invention using the following procedure:—0.25 grams each of di-sodium EDTA and benzethonium chloride were weighed into separate sterile bottles and dissolved in 100 ml of 50:50 (v/v) IDA:SDW and 100% IDA respectively. 50 µg/cm$^2$ of EDTA and 50 µg/cm$^2$ of benzethonium chloride were added to the dressing by carefully pipetting 220 µl of each solution over the entire surface of each dressing sample. The samples were then placed back into the original packaging and dried in a vacuum oven at 90° C. and 0.9 atmospheres of vacuum for approximately 2 hours. A colorimeter was used to prepare a suspension of *Staphylococcus aureus* approximately 1×10$^8$ CFU/ml in MRD (0.16-0.18 OD540) and serially diluted to obtain approximately 1×10$^4$ CFU/ml. Two 100 ml volumes of molten TSA (approximately 45° C.) were each inoculated with 1 ml of the 1×10$^4$ CFU/ml *Staphylococcus aureus* suspension and swirled to mix. 20 ml volumes of this bacterially seeded molten agar were then measured and poured into nine 60 ml pots (with an internal diameter of 3.75 cm). When cooled and set these pots were incubated at 35° C.±3° C. for 4 hours±15 minutes to initiate growth. After 4 hours each of the test dressing was hydrated with 2.5 ml of 0.85% Saline Solution in a sterile Petri dish and placed into a 60 ml pot and onto the surface of the seeded agar. One pot had no dressing applied to act as a positive control. The pots were then incubated for another 24 hours after which time the dressings were removed and disposed of. The pots were then re-incubated for a minimum 72 hours to allow the already established colonies to grow. After the final incubation period the pots were evaluated and photographed next to a calibrated rule.

Results: Where the dressing had imparted an antibacterial effect in the seeded agar beneath the dressing the agar appeared transparent. Where bacterial growth had not been inhibited the agar appeared opaque. The depth of the transparent zone of agar from the surface in contact with the dressing was interpreted as an indication of antimicrobial efficacy. Results are presented in FIG. 2. The positive control was opaque to the surface of the agar, i.e. there was no transparent zone. The results indicate that all of the silver containing dressings tested had some antimicrobial potency, but this varied between dressing types. The addition of this example formulation of the invention increased the depth of the transparent zone by at least a factor of two for all dressing types but the rank order remained the same. This suggested that potency is dependent on dressing type but synergystic enhancement was independent of dressing type.

Figure 2:
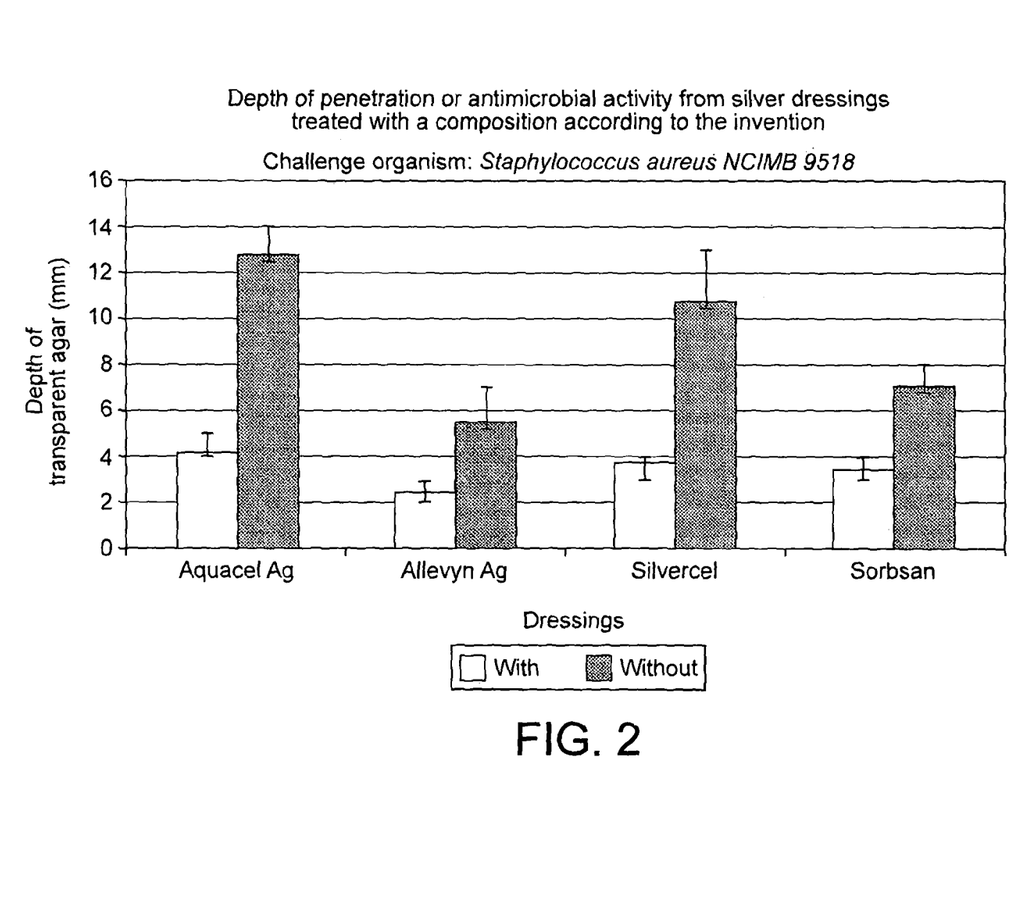
FIG. 2 shows a comparison of the depth of penetration (mm) of antimicrobial action between silver dressings tested both with treatment and without treatment of a composition according to the invention.

The Aquacel Ag had a greater depth of penetration than the other dressings for both the control and treated tests. Aquacel Ag also had the greatest improvement in antimicrobial penetration when treated with a solution according to the invention as the average depth of penetration was three times greater than the control.

EXAMPLE 4

Enhancement of Antimicrobial Efficacy with Different Antimicrobial Metals

Previous Examples using the MBEC (Minimum Biofilm Eradication Concentration) method have shown that the addition of specific antimicrobial agents to silver enhances its antimicrobial activity. The purpose of this example was to assess the effect of these agents on the antimicrobial activity of other metals, using the MBEC method.

Method: A 0.2% w/w aqueous stock solution of the quaternary cationic surfactant didecyl dimethyl ammonium chloride (DDAC) was prepared from a concentrated commercial solution (50% w/v solution, Merck KGaA, Darmstadt, Germany). Individual stock solutions of silver nitrate, copper (II) nitrate trihydrate, gallium (III) nitrate, nickel (II) nitrate hexahydrate, zinc sulphate heptahydrate, manganese (II) chloride tetrahydrate, iron (II) sulphate heptahydrate, iron (III) sulphate hydrate, and copper (II) nitrate trihydrate were prepared from commercially available laboratory solids. Each solution was adjusted to approximately pH 5.5 by the addition of small amounts of dilute aqueous sodium hydroxide and/or dilute hydrochloric acid. The metal ion solutions were then volumetrically diluted to 0.1% w/w (with respect to the metal) with purified water. Any precipitates were kept homogenously suspended by vigorous shaking. The MBEC assay as described in Example 1 was then performed for the surfactant solution alone, each individual metal ion solution and then for each metal solution in combination with the surfactant solution.

Results:

| Metal | pH | MBEC for the metal ion (ppm)† | | Synergy |
|---|---|---|---|---|
| | | Without DDAC | With 0.1% DDAC | |
| Silver | 5.27 | 12.5 | 0.097 | +ve |
| Copper* | 5.47 | 15.6 | 1.95 | +ve |
| Iron (II)* | 5.30 | >1000 | ≤0.24 | +ve |
| Iron (III)* | 5.40 | >1000 | ≤0.24 | +ve |
| Gallium* | 5.51 | >1000 | ≤0.24 | +ve |
| Manganese | 5.40 | >1000 | ≤0.24 | +ve |
| Nickel | 5.51 | >1000 | ≤0.24 | +ve |
| Zinc | 5.40 | >1000 | ≤125 | +ve |
| DDAC | — | 0.2% | -na- | -na- |

†Lowest concentration at which activity was observed; ppm is equivalent to µg/g (or µg/ml in aqueous solutions). These values are approximate.
*These metals formed precipitates when the 0.1% solutions were pH adjusted to pH 5.5; however the precipitate was dissolved when diluted in the test plate.

Literature data for metal solutions (pH unadjusted) suggests the following order in terms of antimicrobial activity:

Silver>Iron>Nickel>Copper>Gallium>Magnesium>Bismuth

The MBEC for DDAC alone was determined as approximately 0.2%. When 0.1% DDAC was used in combination with the listed metal ion solutions all produced a significant reduction in the MBEC for the metal thus demonstrating a synergistic effect which is independent of the identity of antimicrobial metal used.

EXAMPLE 5

The Effect of pH

When used at high concentration many cationic surfactants have antimicrobial activity; typically this is enhanced by an alkaline pH. Similarly, many researchers have found that the activity of some silver compounds is also enhanced by elevated pH. To prevent pain and tissue damage, products applied to broken skin need to be near pH neutral or have slightly acidic in pH. This Example investigates the effect of pH on the synergystic effect between a quaternary cationic surfactant and an antimicrobial metal.

Method: The following aqueous stock solutions were prepared:—benzethonium chloride (1.0% w/w), silver nitrate (0.1% w/w with respect to the metal), sodium acetate (0.5M) and acetic acid (0.5M).

In the control experiment sodium acetate and acetic acid solutions were mixed at various ratios and diluted with purified water to give a range of pH buffer solutions with different pH's but with the same overall ionic strength (0.1M with respect to acetate ion). To each, sufficient silver nitrate solution was added to make the solution 0.01% w/w with respect to silver. Each solution was then challenged in the MBEC method as described in Example 1 to determine if, at this level of pH and silver, the solution was above or below the MBEC. Using a second set of similarly prepared solutions (0.1M acetate buffer, 0.01% silver) a second MBEC experiment was performed in which the concentration of the surfactant solution was varied.

Results: None of the 0.01% silver solutions pH buffered in the range 4.7 to 7.7 were effective against biofilms in the MBEC model. Surfactant concentrations of >0.25%, ≤0.10% and 0.025% were required to eradicate biofilm in the MBEC model at pH 6.9, 6.2 and 5.5 respectively.

This suggests the synergystic antimicrobial effect of the current invention is enhanced by reducing pH (becoming more acidic) which is counter to current wisdom.

EXAMPLE 6

Enhancement of the Antimicrobial Efficacy of a Semi-Solid (Gel) Composition Containing Silver, EDTA and Quaternary Surfactant Previous Examples (1, 2, 4 & 5) illustrate applicability to simple solutions. This example seeks to demonstrate that the addition of inert excipients that modify the physical form and properties of the base active solution have no effect on the observed efficacy. Increasing the viscosity by the addition of the gelling agent hydroxyethylcellulose (HEC, Aqualon type: Natrosol 250HX Pharm) is used in this example with the activity of the formulated gels being compared to the equivalent solution using the MBEC assay as previously described.

Method: Stock solutions of silver nitrate, benzethonium chloride, di-sodium EDTA (pH~4), tri-sodium EDTA (pH~8) and HEC were prepared. These were then combined in various ways to produce a matrix of samples of one, two, three components (EDTA being included only once in any combination) with and without HEC. The final component concentrations being 0%, 0.0001% or 0.02% for silver (Ag); 0%, 0.1% or 1% for benzethonium chloride (BeCl); 0%, 0.2% or 1% for EDTA; 0% or 0.1% for HEC. Test samples were challenged against a microbial biofilm using the MBEC method previously outlined in Example 1. The results were recorded as either effective (no bacterial growth) or ineffective (bacterial growth as indicated by turbidity). All test samples were prepared in duplicate and each MBEC determination was performed in triplicate therefore six assays results were obtained for each sample.

Figure 3:
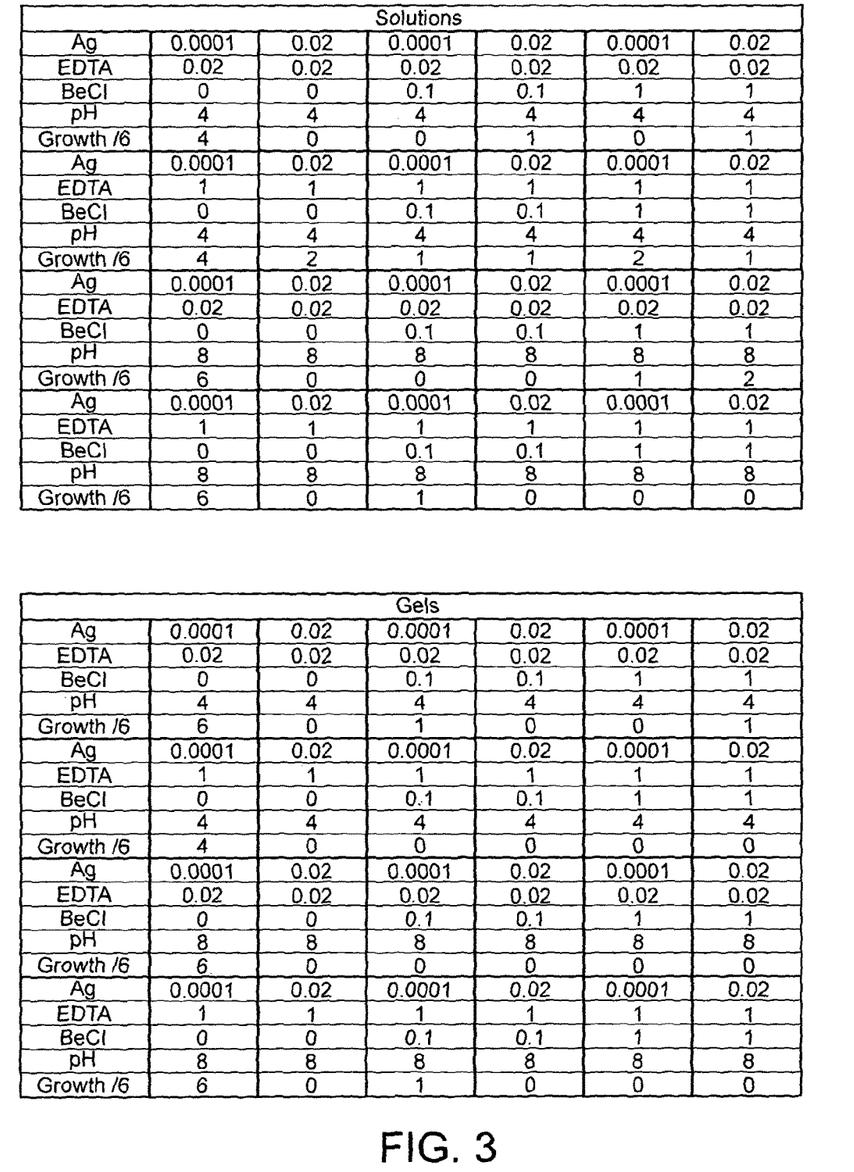
FIG. 3 shows a comparison of the anti-biofilm activity (MBEC data) of solutions and semi-solid gels.

Results:

A summary of the results for combinations are shown in FIG. 3. Adding an inert excipient (HEC) to modify the physical properties of the test substance did not alter the anti-biofilm activity of the test mixture. Synergistic behaviour was still observed for the combinations at pH 4 and pH 8 at the lower end of the preferred concentration ranges. No inhibitory effects of the addition of the inert excipient were observed at the upper end of the preferred concentration ranges.

The invention claimed is:

1. An antimicrobial wound dressing comprising a silver ion from a silver salt, a quaternary cationic surfactant, and ethylenediaminetetra-acetic acid (EDTA) present as the di-, tri- or tetra-basic salt of EDTA at a level of less than 2% by weight, wherein the silver ion is included in the antimicrobial wound dressing at a level of from 0.01% to 10%.

2. A The antimicrobial wound dressing as claimed in claim 1 having a pH of 4 to 8.

3. The antimicrobial wound dressing as claimed in claim 1 wherein the quaternary cationic surfactant is a quaternary ammonium surfactant.

4. The antimicrobial wound dressing as claimed in claim 1 wherein the quaternary cationic surfactant is selected from the group of the salts where the cation is benzethonium, benzalkonium, dimethyldiakylonium, alkylpyridinium and alkyltrimethylammonium.

5. A process for making an antimicrobial wound dressing comprising:
    (i) obtaining an absorbent wound dressing, and
    (ii) treating the absorbent wound dressing such that the absorbent wound dressing contains a silver ion from a silver salt, a quaternary cationic surfactant, and ethylenediaminetetra-acetic acid (EDTA) present as the di-, tri- or tetra-basic salt of EDTA at a level of less than 2% by weight,
   wherein the silver ion is included in a composition at a level of from 0.0001% to 0.02% by weight if the composition is in aqueous solution, or if the silver ion is included in the composition at a level of from 0.01% to 10% by weight.

6. The antimicrobial wound dressing as claimed in claim 1 having a pH of between 4 and 7.

7. The antimicrobial wound dressing as claimed in claim 1 having a pH of between 4.5 and 5.5.

8. The antimicrobial wound dressing as claimed in claim 1 wherein the EDTA is present at a level from 0.2% to 1% by weight.

9. The antimicrobial wound dressing as claimed in claim 1 wherein the quaternary cationic surfactant is present at a level of more than or equal to 0.025% by weight.

10. The antimicrobial wound dressing as claimed in claim 1 wherein the quaternary cationic surfactant is present at a level of between 0.05% and 4% by weight.

11. The antimicrobial wound dressing of claim 1 further comprising a buffering agent.

12. The antimicrobial wound dressing of claim 11 wherein the buffering agent is present in an amount of about 0.5% to 2% by weight.

13. The antimicrobial wound dressing of claim 11 wherein the buffering agent is selected from the group comprising citric acid/di-sodium hydrogen phosphate, citric acid/sodium citrate and acetic acid/sodium acetate.

14. The antimicrobial wound dressing of claim 7 wherein the pH is around 5.5.

15. The process of claim 5, wherein the quaternary cationic surfactant is selected from the group of the salts where the cation is benzethonium, benzalkonium, dimethyldiakylonium, alkylpyridinium and alkyltrimethylammonium.

16. The process of claim 5, wherein the quaternary cationic surfactant is present at a level of more than or equal to 0.025% by weight.

17. The process of claim 5, wherein the quaternary cationic surfactant is present at a level of between 0.05% and 4% by weight.

* * * * *